United States Patent

Monsees et al.

(10) Patent No.: US 6,476,246 B2
(45) Date of Patent: Nov. 5, 2002

(54) BIDENTATE PHOSPHORUS LIGANDS AND THEIR USE IN CATALYSIS

(75) Inventors: Axel Monsees, Frankfurt; Uwe Dingerdissen, Seeheim-Jugenheim; Sabine Laschat, Braunschweig; Thorsten Sell, Ruhr, all of (DE)

(73) Assignee: Degussa AG, Duesseldorf (DE)

( * ) Notice: Subject to any disclaimer, the term of this patent is extended or adjusted under 35 U.S.C. 154(b) by 0 days.

(21) Appl. No.: 09/983,343

(22) Filed: Oct. 24, 2001

(65) Prior Publication Data

US 2002/0095049 A1 Jul. 18, 2002

(30) Foreign Application Priority Data

Oct. 25, 2000 (DE) .......................................... 100 52 868

(51) Int. Cl.$^7$ ................................................. C07F 9/00
(52) U.S. Cl. .............................. 556/19; 558/155; 568/6
(58) Field of Search ................................ 568/8, 13, 15; 558/70, 155; 556/13, 19, 20; 502/162, 165, 166

(56) References Cited

PUBLICATIONS

CA:127:161552 abs of J Mol Catal A Chem. by Chelucci et al 122(2–3) pp. 111–114 1997.*
CA:134:207970 abs of European Journal of Organic Chemistry by Sell et al (24) pp 4119–4124 Dec. 2000.*
CA:126:171722 abs of Tetrahedron Asymmetry by Komarov et al 8(3) pp 435–445 1997.*
CA:133:222989 abs of Terahedron Asymmetry by Li et al 11(10)pp 2077–2082 2000.*
CA:115:514630 abs of Izv Akad. Nauk. SSSR, Ser. Khim. by Zhorov et al (5) pp 983–9 1991.*
CA:105:226793 abs of J Organometl. Chem by Neuffer et al 301(3) pp 389–97 1986.*
CA:90:86616 abs of Chim Ind. (milan) by Piacenti et al 60(10) pp808–9 1978.*
I.V. Komarov, et al., Tetrahedron: Asymmetry, vol. 8, No. 3, pp. 435–445, "Synthesis Of Chiral Functionalized Phosphine Ligands Based On Camphor Skeleton", Feb. 6, 1997.
T. Sell, et al., European Journal of Organic Chemistry, Bd. 2000, No. 24, pp. 4119–4124, "A Concise EX Chiral Pool Approach To Novel Bidentate Camphane Phosphane Ligands", Dec. 4, 2000.
*Neue Verbindungen Der Terpenreihe Und Verwandter Systeme*, F. Dallacker, I. Alroggen, H. Krings, B. Laurs and M. Lipp, Liebigs Ann. Chem. 1961, pp. 23–36.
*Anwendung Der Wittig–Reaktion Auf Bi–Und Tricyclische Terpene*, F. Dallacker, K. Ulrichs and M. Lipp, Liebigs Ann. Chem. 1963, pp. 50–55.
*Reduction of Sulfonic Acids and Related Organosulfur Compounds wiht Triphenylphosphine–Iodine System*, S. Oae and H. Togo, Bull. Chem. Soc. Jpn. 1983, vol. 56, No. 12, pp. 3802–3812.
*Über 10–Halogenborneole*, N. Proth, Rev. Technique Luxembourgeoise 1976, pp. 195–199.

* cited by examiner

Primary Examiner—Jean F. Vollano
(74) Attorney, Agent, or Firm—Oblon, Spivak, McClelland, Maier & Neustadt, P.C.

(57) ABSTRACT

Chiral, unsymmetrical bidentate organophosphorus ligands of the formula (I) are reacted with transition metal centers to form complexes with catalytic activity. The compounds contain chiral bicycloaliphatic skeletons. Synthesis of the bidentate ligands proceeds from norbornyl derivatives.

(I)

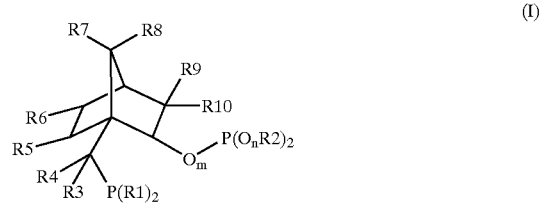

17 Claims, No Drawings

US 6,476,246 B2

BIDENTATE PHOSPHORUS LIGANDS AND THEIR USE IN CATALYSIS

BACKGROUND OF THE INVENTION

Field of the Invention

The present invention relates to novel unsymmetrical chiral diphosphines and phosphine phosphinites and their synthesis and to complexes of these compounds with metals of groups VIIb, VIIIb and Ib of the Periodic Table and also to their use as catalysts for enantioselective transformations, in particular hydrogenations.

DISCUSSION OF THE RELATED ART

Trisubstituted organophosphorus compounds are of great importance as ligands in homogeneous catalysis. Variation of the substituents of phosphorus in such compounds enables the electronic and steric properties of the phosphorus ligands to be influenced in a tailored manner, so that selectivity and activity in homogeneously catalyzed processes can be controlled.

Enantiomerically enriched chiral ligands are used in asymmetric synthesis or asymmetric catalysis, where the important aspect is that the electronic and stereochemical properties of the ligand are optimally matched to the respective catalysis problem. There is therefore a great need for chiral ligands which are stereochemically and electronically different in order to find the optimum "tailored" ligand for a particular asymmetric catalysis.

The structural variety of phosphorus ligands known hitherto is very wide. These ligands can be classified, for example, according to class of substance and examples of such classes of substances are trialkylphosphines and triarylphosphines, phosphites, phosphinites, phosphonites, aminophosphines, etc. This classification according to class of substance is particularly useful for describing the electronic properties of the ligands.

Phosphorus ligands can also be classified according to their symmetry properties or according to the denticity of the ligands. This structuring takes account, in particular, of the stability, activity and stereoselectivity of metal complexes with phosphorus ligands as catalyst precursors or as catalysts. Apart from the widespread $C_2$-symmetrical bidentate ligand systems such as DUPHOS, DIPAMP, BINAP or DEGUPHOS, unsymmetrical bidentate organophosphorus ligands are increasingly becoming the focus of asymmetric catalysis. Important examples are the large class of versatile chiral ferrocenylphosphine ligands such as JOSIPHOS, DPPM, the bisphosphinite ligands such as CARBOPHOS which are used particularly successfully in the asymmetric hydrogenation of olefins and imines, or the phosphine phosphite ligands such as BINAPHOS or BIPHEMPHOS which are used successfully in the asymmetric hydroformylation of olefins.

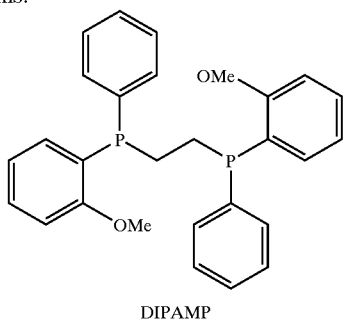

DIPAMP

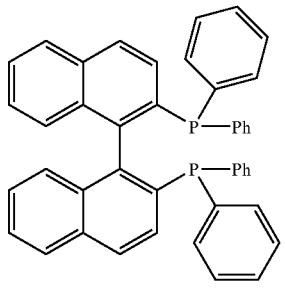

BINAP

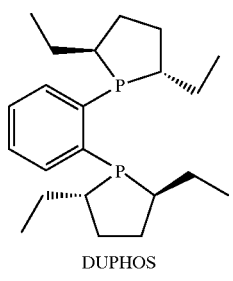

DUPHOS

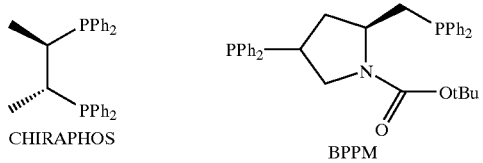

CHIRAPHOS     DEGUPHOS     BPPM

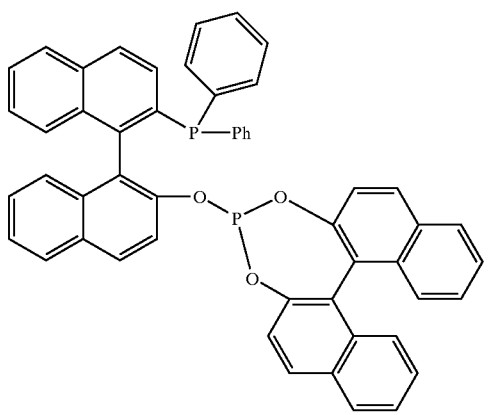

BINAPHOS

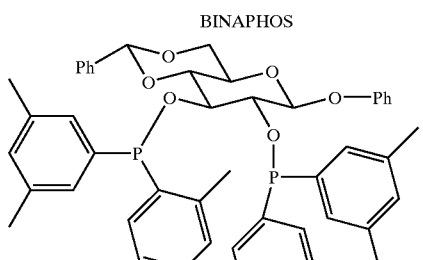

CARBOPHOS

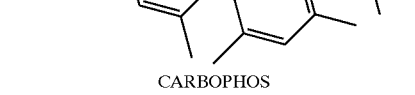

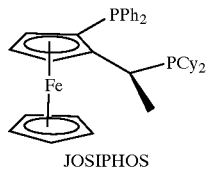

JOSIPHOS

An important aspect of the success of these classes of compound is believed to be the creation of a particularly asymmetric environment around the metal center by these ligand systems. To utilize such an environment for an effective transfer of chirality, it is advantageous to control the flexibility of the ligand system as inherent limitation of the asymmetric induction.

Disadvantages of the chiral phosphorus ligand systems known hitherto are, firstly, their complicated synthesis and, secondly, the restricted opportunities for varying the properties of a given ligand skeleton, e.g. by the introduction of different substituents.

SUMMARY OF THE INVENTION

It is an object of the present invention to provide novel, unsymmetrical, bidentate and chiral phosphorus ligand systems which can easily be varied in terms of their steric and electronic properties over an extraordinarily wide range.

This object is achieved by a class of chiral, unsymmetrical bidentate organophosphorus compounds of the formula (I) in which a chiral bicycloaliphatic skeleton is present.

The present invention accordingly provides compounds of the formula (I),

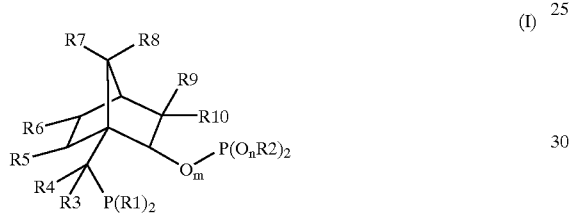

where
m and n may each be, independently of one another, 0 or 1 and
R1–R2 are, independently of one another, a radical selected from the group consisting of $C_1$–$C_{24}$-alkyl, $C_3$–$C_8$-cycloalkyl which may contain 1–2 heteroatoms selected from the group consisting of N, O and S, $C_6$–$C_{14}$-aryl, phenyl, naphthyl, fluorenyl and $C_2$–$C_{13}$-heteroaryl in which the number of heteroatoms selected from the group consisting of N, O and S may be 1–4.
The cyclic aliphatic or aromatic radicals are preferably 5- and 6-membered rings.
The abovementioned radicals may themselves each be monosubstituted or polysubstituted. These substituents may be, independently of one another, hydrogen, $C_1$–$C_{20}$-alkyl, $C_2$–$C_{20}$-alkenyl, $C_1$–$C_{10}$-haloalkyl, $C_3$–$C_8$-cycloalkyl, $C_2$–$C_9$-heterocycloalkyl, $C_6$–$C_{10}$-aryl, phenyl, naphthyl, fluorenyl, $C_2$–$C_6$-heteroaryl in which the number of heteroatoms, in particular from the group consisting of N, O and S, may be 1–4, $C_1$–$C_{10}$-alkoxy, preferably OMe, $C_1$–$C_9$-trihalomethylalkyl, preferably trifluoromethyl and trichloromethyl, halo, in particular fluoro and chloro, nitro, hydroxy, trifluoromethylsulfonato, oxo, amino, $C_1$–$C_8$-substituted amino of the formulae NH-alkyl-$C_1$–$C_8$, NH-aryl-$C_5$–$C_6$, N-alkyl$_2$-$C_1$–$C_8$, N-aryl$_2$-$C_5$–$C_6$, N-alkyl$_3$-$C_1$–$C_8^+$, N-aryl$_3$-$C_5$–$C_6^+$, NH—CO-alkyl-$C_1$–$C_8$, NH—CO-aryl-$C_5$–$C_6$, cyano, carboxylato of the formulae COOH and COOQ, where Q is either a monovalent cation or $C_1$–$C_8$-alkyl, $C_1$–$C_6$-acyloxy, sulfinato, sulfonato of the formulae $SO_3H$ and $SO_3Q$, where Q is either a monovalent cation, $C_1$–$C_8$-alkyl or $C_6$-aryl, phosphato of the formulae $PO_3H_2$, $PO_3HQ$ and $PO_3Q_2$, where Q is either a monovalent cation, $C_1$–$C_8$-alkyl or $C_6$-aryl, tri-$C_1$–$C_6$-alkylsilyl, in particular SiMe$_3$, and/or where two radicals $R^1$ or two radicals $R^2$ may be connected to one another, preferably forming a 4–8-membered ring which may be substituted by linear or branched $C_1$–$C_{10}$-alkyl, $C_6$-aryl, benzyl, $C_1$–$C_{10}$-alkoxy, hydroxy or benzyloxy.

R3–R10 are each, independently of one another, a hydrogen atom or a radical selected from the group consisting of $C_1$–$C_{24}$-alkyl, $C_1$–$C_{10}$-haloalkyl, $C_3$–$C_8$-cycloalkyl, $C_3$–$C_8$-cycloalkenyl which may also contain 1–2 heteroatoms selected from the group consisting of N, O and S, $C_6$–$C_{14}$-aryl, phenyl, naphthyl, fluorenyl and $C_2$–$C_{13}$-heteroaryl in which the number of heteroatoms selected from the group consisting of N, O and S may be 1–4.
The cyclic aliphatic or aromatic radicals here are preferably 5- to 7-membered rings.
The abovementioned groups may themselves each be monosubstituted or polysubstituted. The substituents may be selected independently from the group consisting of hydrogen, $C_1$–$C_{20}$-alkyl, $C_2$–$C_{20}$-alkenyl, $C_3$–$C_8$-cycloalkyl, $C_3$–$C_8$-cycloalkenyl, $C_2$–$C_9$-heteroalkyl, $C_1$–$C_9$-heteroalkenyl, $C_6$–$C_{10}$-aryl, $C_1$–$C_{10}$-haloalkyl, phenyl, naphthyl, fluorenyl, $C_2$–$C_6$-heteroaryl in which the number of heteroatoms, in particular from the group consisting of N, O and S, may be 1–4,
$C_1$–$C_{10}$-alkoxy, trichloromethyl, fluoro, oxo, amino, $C_1$–$C_8$-substituted amino of the formulae N-alkyl$_2$-$C_1$–$C_8$, N-aryl$_2$-$C_5$–$C_6$, N-alkyl$_3$-$C_1$–$C_8^{+,}$ N-aryl$_3$-$C_5$–$C_6^+$,
and where R5 and R6 may be connected so as to form a 5–7-membered cyclic aromatic or aliphatic compound.

P is trivalent phosphorus.
The invention also provides complexes comprising a chiral bidentate organophosphorus ligand of the formula (I) with at least one metal. Such complexes are obtainable by simple mixing of the organophosphorus compounds of the invention with metal complex precursors in solution.
It is preferred that
R1–R2, are each, independently of one another, a radical selected from the group consisting of $C_1$–$C_6$-alkyl, $C_5$–$C_6$-cycloalkyl, $C_6$-aryl, phenyl, naphthyl, $C_4$–$C_5$-heteroaryl in which the number of heteroatoms selected from the group consisting of N, O and S is 1, where the abovementioned aromatic or heteroaromatic groups may themselves each be monosubstituted to trisubstituted. The substituents may be selected independently from the group consisting of hydrogen, $C_1$–$C_6$-alkyl, $C_2$–$C_4$-alkenyl, $C_1$–$C_6$-haloalkyl, $C_2$–$C_6$-heteroalkyl, $C_6$-aryl, phenyl, naphthyl, fluorenyl, $C_3$–$C_5$-heteroaryl, in which the number of heteroatoms selected from the group consisting of N, O and S may be 1–2, $C_1$–$C_6$-alkoxy, preferably OMe, $C_1$–$C_9$-trihalomethylalkyl, preferably trifluoromethyl and trichloromethyl, halo, in particular fluoro and chloro, nitro, hydroxy, trifluoromethylsulfonato, oxo, amino, $C_1$–$C_6$-substituted amino of the formulae $NH_2$, NH-alkyl-$C_1$–$C_6$, NH-aryl-$C_6$, N-alkyl$_2$-$C_1$–$C_6$, N-aryl$_2$-$C_6$, N-alkyl$_3$-$C_1$–$C_6^+$, N-aryl$_3$-$C_6^+$, NH—CO-alkyl-$C_1$–$C_6$, NH—CO-aryl-$C_6$, in particular NMe$_2$, NEt$_2$, cyano, carboxylato of the formulae COOH and COOQ, where Q is either a monovalent cation or $C_1$–$C_4$-alkyl, $C_1$–$C_6$- acyloxy, sulfinato, sulfonato of the formulae SO$_3$H and SO$_3$Q, where Q is either a monovalent cation, C$_1$–C$_4$-alkyl or C$_6$-aryl, phosphato of the formulae PO$_3$H$_2$, PO$_3$HQ and PO$_3$Q$_2$, where Q is either a monovalent cation, C$_1$–C$_4$-alkyl or C$_6$-aryl, tri-C$_1$–C$_6$-alkylsilyl, in particular SiMe$_3$.

R1–R10 in the ligand system of the invention preferably contain, independently of one another, alkyl, alkenyl, cycloalkyl, alkoxy, trialkylsilyl or/and dialkylamino groups which each contain from 1 to 20, in particular from 1 to 6, carbon atoms.

Among the group of alkyl substituents, preference is given to methyl, ethyl, n-propyl, 1-methylethyl, n-butyl, 1-methylpropyl, 1,1-dimethylethyl, n-pentyl, 1-methylbutyl, 2-methylethyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, n-heptyl, n-octyl, n-nonyl, n-decyl.

Among cyclic alkyl substituents, particular preference is given to substituted and unsubstituted cyclopentyl, cyclohexyl and cycloheptyl radicals.

Preferred alkenyl substituents are vinyl, propenyl, isopropenyl, 1-butenyl, 2-butenyl, 1-pentenyl, 2-pentenyl, 2-methyl-1-butenyl, 2-methyl-2-butenyl, 3-methyl-1-butenyl, 1-hexenyl, 1-heptenyl, 2-heptenyl, 1-octenyl or 2-octenyl. Among cyclic alkenyl substituents, particular preference is given to cyclopentenyl, cyclohexenyl, cycloheptenyl and norbornyl.

As aryl substituents in R$^1$–R$^2$, particular preference is given to 2-alkylphenyl, 3-alkylphenyl, 4-alkylphenyl, 2,6-dialkylphenyl, 3,5-dialkylphenyl, 3,4,5-trialkylphenyl, 2-alkoxyphenyl, 3-alkoxyphenyl, 4-alkoxyphenyl, 2,6-dialkoxyphenyl, 3,5-dialkoxyphenyl, 3,4,5-trialkoxyphenyl, 3,5-dialkyl-4-alkoxyphenyl, 3,5-dialkyl-4-dialkylaminophenyl, 4-dialkylamino, where the abovementioned alkyl and alkoxy groups preferably each contain from 1 to 6 carbon atoms, 3,5-trifluoromethyl, 4-trifluoromethyl, 2-sulfonyl, 3-sulfonyl, 4-sulfonyl, monohalogenated to tetrahalogenated phenyl and naphthyl.

Preferred halogen substituents are F, Cl and Br.

All haloalkyl or/and haloaryl groups preferably have the formulae CHal$_3$, CH$_2$CHal$_3$, C$_2$Hal$_5$, where Hal may be, in particular F, Cl or Br. Particular preference is given to haloalkyl or/and haloaryl groups of the formulae CF$_3$, CH$_2$CF$_3$, C$_2$F$_5$.

Finally, preference is given to optically active ligand systems of the formula (I) which are enriched in one enantiomer. Particular preference is given to ligand systems in which the enantiomeric enrichment exceeds 90%, in particular 99%.

The class of bidentate organophosphorus compounds provided by the invention has a chiral ligand skeleton which is simple to modify in a variety of ways and can be varied within a very wide range in respect of its steric and electronic properties by the simple introduction of widely differing substituents. In metal complexes, organophosphorus compounds of the formula (I) are able to create a highly asymmetric coordination sphere with independently modifiable organophosphorus donors on the metal center and thus make effective asymmetric induction possible. In addition, the flexibility of the coordination sphere of the complex can be controlled in steric terms via the easy introduction of a wide variety of substituents into the organophosphorus ligands.

Thus, a wide range of applications is possible for the compounds of the formula (I) since the bidentate phosphorus ligands can be optimized sterically and electronically according to the catalytic synthesis by the introduction of suitable substituents.

At the same time, the compounds of the invention can, in contrast to many established ligand systems, be synthesized particularly simply in a wide range of variations from simple starting materials. This makes it possible for the ligands of the present invention to be prepared industrially without problems.

Various methods using readily obtainable starting materials are available for the synthesis of compounds of the formula (I).

Phosphorus compounds according to the invention from the class of phosphines phosphinites can be prepared, for example, as follows:

Starting from a 10-camphorsulfonic acid derivative, the salt of the camphorsulfonic acid derivative can firstly be prepared in an aqueous basic medium and the sulfonic acid radical can then be replaced by a halide radical in the presence of a phosphorus trihalide. In an alternative method, the replacement of the sulfonic acid radical by a halide radical is carried out in a single-step synthesis in the presence of molecular halogen and PR$_3$. Preferred phosphorus trihalides are PBr$_3$ and PI$_3$, preferred molecular halogens are Br$_2$ and I$_2$. Subsequent reduction gives the corresponding isoborneol derivative. In further process steps, the hydroxy group of the camphor derivative is silylated and subsequently phosphinated in the 10 position with replacement of the halogen by means of an alkali metal salt of a phosphine AP(R1)$_2$. The phosphine group is protected by addition of a borane adduct. Removal of the protective group from the hydroxy group is carried out by customary methods, e.g. by addition of tetrabutylammonium fluoride (TBAF). The hydroxy group is then phosphinated in a basic medium by addition of a phosphine halide HalP(R2)$_2$. The newly introduced second phosphorus-containing group can likewise be protected by addition of a borane adduct. The removal of the protective borane groups is carried out using a nitrogen base. The phosphine phosphinites of the invention are obtained.

The diphosphines can be prepared from the corresponding phosphine phosphinites by rearrangement of the phosphinite group to the phosphine oxide by heating and subsequent reduction to the diphosphine.

The choice of an appropriate preparative method depends on the availability of the corresponding starting materials and on the desired substitution pattern.

The abovementioned processes will be described in more detail below with the aid of general preferred process examples.

Monosubstituted bicyclic skeletons are available from the chiral pool. 10-bromocamphor is prepared in a three-stage process, as described above, based on literature methods ((a) F. Dallacker, I. Alroggen, H. Krings, B. Laurs, M. Lipp, Liebigs Ann. Chem. 1961, 647, 23–36; (b) F. Dallacker, K. Ulrichs, M. Lipp, Liebigs Ann. Chem. 1963, 667, 50–55; (c) N. Proth, Rev. Tech. Lux 1976, 4, 195–199).

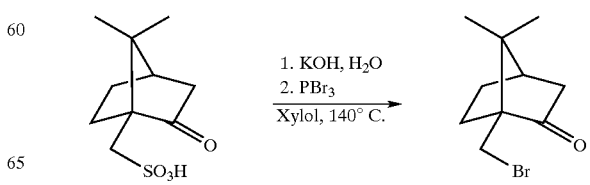

A more advantageous synthetic method is a single-stage synthesis of 10-iodocamphor from 10-camphorsulfonic acid (S. Oae, H. Togo, *Bull. Chem. Soc. Jpn.* 1983, 56, 3802–3812), followed by a selective reduction of the carbonyl group using lithium aluminum hydride to give the iodoalcohol.

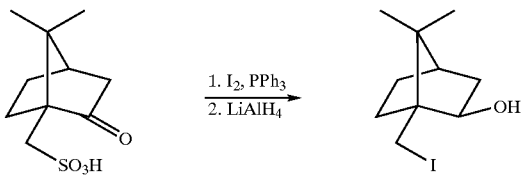

The free hydroxy group is protected by a protective silyl group by addition of Et$_3$SiCl in the presence of a base, and the side chain is subsequently phosphinated using lithium salts of dialkylphosphines or diarylphosphines. All of the abovementioned radicals R1 can be introduced selectively by choice of an alkali metal salt of an appropriate phosphine. The phosphine is converted into the borane complex by means of a borane THF adduct and desilylation using TBAF gives the hydroxyphosphine in high yields.

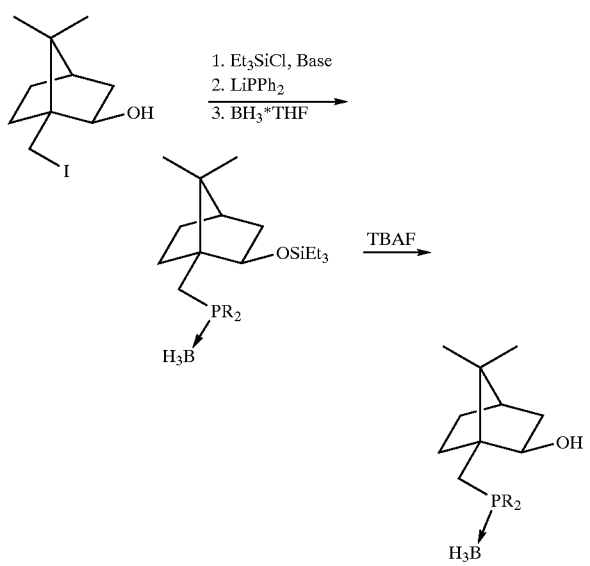

The introduction of the second phosphine unit is achieved by deprotonation of the hydroxy group and reaction with a chlorophosphine to selectively introduce the group P(O$_n$R2)$_2$. The phosphine phosphinite can likewise be converted into the borane complex by means of a borane-THF adduct. Decomplexation is carried out by addition of a nitrogen base.

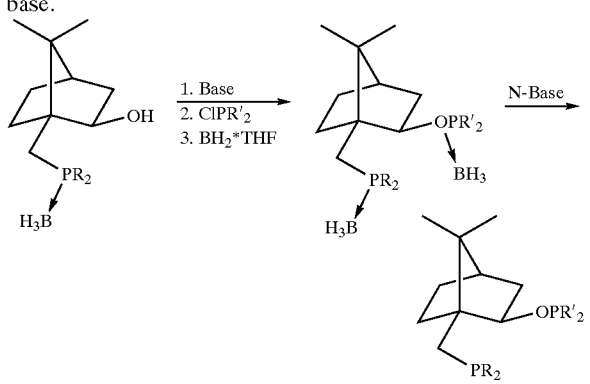

To prepare the diphosphines, the phosphine phosphinites are rearranged thermally in solution at a temperature of from 100° C. to 200° C. with the inversion of the stereochemistry to give the phosphine oxide. Subsequent reduction gives the diphosphine.

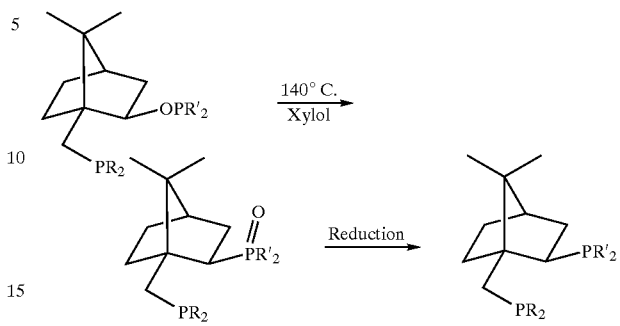

The compounds of the formula (I) can be used as ligands on metals in asymmetric, metal-catalyzed reactions (e.g. hydrogenation, hydroformylation, rearrangement, allylic alkylation, cyclopropanation, hydrosilylation, hydride transfers, hydroborations, hydrocyanations, hydrocarboxylations, aldol reactions or the Heck reaction) and also in polymerizations. They are particularly useful for asymmetric reactions.

Suitable complexes, in particular those of the formula (II), contain novel compounds of the formula (I) as ligands.

$$[M_xP_yL_zS_q]A_r \qquad (II)$$

In the formula (II), M is a transition metal center, L are identical or different coordinating organic or inorganic ligands and P are novel bidentate organophosphorus 20 ligands of the formula (I), S are coordinating solvent molecules and A are equivalents of noncoordinating anions, where x is 1 or 2, y is an integer greater than or equal to 1 and z, q and r are, independently of one another, integers greater than or equal to 0.

The upper limit on the sum y+z+q is imposed by the number of coordination centers available on the metal centers, with not all coordination sites having to be occupied. Preference is given to complexes having an octahedral, pseudooctahedral, tetrahedral, pseudotetrahedral or square planar coordination sphere, which may also be distorted, around the respective transition metal center. In such complexes, the sum y+z+q is smaller than or equal to 6x.

The complexes of the invention contain at least one metal atom or ion, preferably a transition metal atom or ion, in particular selected from the group consisting of palladium, platinum, rhodium, ruthenium, osmium, iridium, cobalt, nickel or/and copper.

Preference is given to complexes having less than four metal centers, particularly preferably those having one or two metal centers. The metal centers can be occupied by different metal atoms and/or ions.

Preferred ligands L in such complexes are halide, in particular Cl, Br and I, diene, in particular cyclooctadiene, norbornadiene, olefin, in particular ethylene and cyclooctene, acetato, trifluoroacetato, acetylacetonato, allyl, methallyl, alkyl, in particular methyl and ethyl, nitrile, in particular acetonitrile and benzonitrile, and also carbonyl and hydrido ligands.

Preferred coordination solvents S are amines, in particular triethylamine, alcohols, in particular methanol, and aromatics, in particular benzene and cumene.

Preferred noncoordinating anions A are trifluoroacetate, trifluoromethanesulfonate, BF$_4$, ClO$_4$, PF$_6$, SbF$_6$ and BAr$_4$.

In the individual complexes, the different molecules, atoms or ions of the individual constituents M, P, L, S and A may be present.

Among complexes having an ionic structure, preference is given to compounds of the type [RhP(diene)]⁺A⁻, where P is a novel ligand of the formula (I).

These metal-ligand complexes can be prepared in situ by reaction of a metal salt or a corresponding precursor complex with the ligands of the formula (I). It is also possible to obtain a metal-ligand complex by reaction of a metal salt or a corresponding precursor complex with the ligands of the formula (I) and subsequent isolation. Such a complex is preferably produced in a single-vessel reaction while stirring at elevated temperature. Catalytically active complexes can also be produced directly in the reaction mixture of the planned catalytic reaction.

Examples of metal salts are metal chlorides, bromides, iodides, cyanides, nitrates, acetates, acetylacetonates, hexafluoroacetylacetonates, tetrafluoroborates, perfluoroacetates or triflates, in particular of palladium, platinum, rhodium, ruthenium, osmium, iridium, cobalt, nickel or/and copper. Examples of precursor complexes are: cyclooctadienepalladium chloride, cyclooctadienepalladium iodide, 1,5-hexadienepalladium chloride, 1,5-hexadienepalladium iodide,bis(dibenzylideneacetone)palladium, bis(acetonitrile)palladium(II) chloride, bis(acetonitrile)palladium(II) bromide, bis(benzonitrile)palladium(II) chloride, bis(benzonitrile)palladium(II) bromide, bis(benzonitrile)palladium(II) iodide,bis(allyl)palladium, bis(methallyl)palladium, allylpalladium chloride dimer, methallylpalladium chloride dimer, tetramethylethylenediaminepalladium dichloride, tetramethylethylenediaminepalladium dibromide, tetramethylethylenediaminepalladium diiodide, (tetramethylethylenediamine)dimethylpalladium, cyclooctadieneplatinum chloride, cyclooctadieneplatinum iodide, 1,5-hexadieneplatinum chloride, 1,5-hexadieneplatinum iodide, bis(cyclooctadiene)platinum, potassium ethylenetrichloroplatinate, cyclooctadienerhodium(I) chloride dimer, norbornadienerhodium(I) chloride dimer, 1,5-hexadienerhodium(I) chloride dimer, tris(triphenylphosphine)rhodium(I) chloride, hydridocarbonyltris(triphenylphosphine)rhodium(I) chloride, bis(cyclooctadiene)rhodium(I) perchlorate, bis(cyclooctadiene)rhodium(I) tetrafluoroborate, bis(cyclooctadiene)rhodium(I) triflate, bis(acetonitrile)cyclooctadienerhodium(I) perchlorate, bis(acetonitrile)cyclooctadienerhodium(I) tetrafluoroborate, bis(acetonitrile)cyclooctadienerhodium(I) triflate, cyclopentadienylrhodium(III) chloride dimer, pentamethylcyclopentadienylrhodium(III) chloride dimer, (cyclooctadiene)Ru($\eta^3$-allyl)$_2$, ((cyclooctadiene)Ru)$_2$(acetate)$_4$, ((cyclooctadiene)Ru)$_2$ (trifluoroacetate)$_4$, RuCl$_2$(arene) dimer, tris(triphenylphosphine)ruthenium(II) chloride, cyclooctadieneruthenium(II) chloride, OsCl$_2$(arene) dimer, cyclooctadieneiridium(I) chloride dimer, bis(cyclooctene)iridium(I) chloride dimer,bis(cyclooctadiene) nickel, (cyclododecatriene)nickel, tris(norbornene)nickel, nickel tetracarbonyl, nickel(II) acetylacetonate, (arene)copper triflate, (arene)copper perchlorate, (arene)copper trifluoroacetate, cobalt carbonyl.

The complexes based on one or more metals, in particular metals selected from the group consisting of Ru, Co, Rh, Ir, Ni, Pd, Pt, Cu, may themselves be catalysts or can be used for preparing catalysts based on one or more metals, in particular metals selected from the group consisting of Ru, Co, Rh, Ir, Ni, Pd, Pt, Cu. All these complexes are particularly suitable for the asymmetric hydrogenation of C=C, C=O or C=N bonds in which they display high activities and selectivities and for asymmetric hydroformylation. In particular, it is advantageous that the ligands of the formula (I) can be very readily matched to the respective substrate and the catalytic reaction in steric and electronic terms due to the wide variety of modifications which are readily possible.

Corresponding catalysts comprise at least one of the complexes of the invention.

In view of the teachings herein one of ordinary skill in the art can prepare the invention complexes and catalysts.

German application 100 52 868.6, filed on Oct. 25, 2000, is incorporated herein by reference in its entirety.

EXAMPLES

General

Reactions of air-sensitive compounds were carried out in an argon-filled glove box or in standard Schlenk tubes. Tetrahydrofuran (THF), diethyl ether and dichloromethane solvents were degassed and dried by filtration through an activated aluminum oxide column using a solvent of a drying unit (Innovative Technologies); toluene and pentane were additionally freed of oxygen by passing them through a column filled with copper catalyst.

The following examples serve to illustrate the invention, although they do not constitute any restriction.

Example 1

(1S)-10-iodocamphor 120 mmol of iodine are added to a solution of 40 mmol of (1S)-camphor-10-sulfonic acid and 200 mmol of triphenylphosphine in 400 ml of toluene and the solution is refluxed for 15 hours. After cooling to room temperature, the solution is washed twice with 100 ml of water and dried. After removal of the solvent, the crude product is purified by means of chromatography and the product is obtained in a yield of 85%.

$^1$H NMR (CDCl$_3$): δ=0.90 (s, 3H), 1.08 (s, 3H), 1.46–1.33 (m, 1H), 1.67–1.55 (m, 6H), 1.91 (d, 1H), 2.06–1.95 (m, 2H), 2.16 (dd, 1H), 2.40 (ddd, 1H), 3.12 (d, 1H), 3.31 (d, 1H) ppm.

Example 2

(1S,2R)-10-iodoisoborneol 24.4 mmol of 10-iodocamphor in 60 ml of ether are added dropwise to a suspension of 17.0 mmol of lithium aluminum hydride in 20 ml of ether while cooling in an ice bath. The reaction mixture is stirred for 2 hours in the ice bath and subsequently for a further 2 hours at room temperature. The reaction mixture is hydrolyzed while cooling in ice and the organic phase is separated off. The aqueous phase is extracted three times with ether and three times with dichloromethane, the combined organic phases are washed with sodium chloride solution, dried and the solvent is removed under reduced pressure. Purification by means of chromatography gives the product in a yield of 84%.

$^1$H NMR (CDCl$_3$): δ=0.86 (s, 3H), 1.06 (m, 4H), 1.26 (ddd, 1H), 1.54 (ddd, 1H), 1.77–1.66 (m, 2H), 1.83 (ddd, 1H), 2.02 (dd, 1H), 2.12 (d, 1H), 3.18 (d, 1H), 3.45 (d, 1H), 3.78 (ddd, 1H) ppm.

Example 3

(1S,2R)-2-Triethylsiloxy-10-iodobornane 7.83 mmol of triethylchlorosilane are added dropwise to a cooled solution of 7.14 mmol of 10-iodoisoborneol and 8.52 mmol of imidazole in 10 ml of DMF and the solution is stirred for 15 minutes in an ice bath and subsequently for a further 14 hours at room temperature. The reaction mixture is hydrolyzed with water, diluted with dichloromethane and the aqueous phase is subsequently extracted four times with dichloromethane. After drying and purification, the product is obtained in a yield of 96%.

$^1$H NMR (CDCl$_3$): δ=0.52 (q, 2H), 0.64 (q, 4H), 0.86 (s, 3H), 0.93 (t, 3H), 0.98 (t, 6H), 1.01–0.95 (m, 1H), 1.04 (s, 3H), 1.22 (ddd, 1H), 1.51 (m, 3H), 1.80–1.73 (m, 1H), 2.01 (dd, 1H), 3.14 (d, 1H), 3.49 (d, 1H), 3.74 (dd, 1H), 3.49 (d, 1H), 3.74 (dd, 1H) ppm.

Example 4

(1 S,2R)-10-Boranatodiphenylphosphino-2-trimethylsilyloxy-bornane

2-Triethylsiloxy-10-iodobornane is added dropwise to a cooled solution of the lithium salt of diphenylphosphine in 6 ml of THF and the mixture is stirred for a further 30 minutes in an ice bath. The solution is subsequently stirred at room temperature for 30 minutes and refluxed for 1 hour. After cooling to 0° C., 5.80 mmol of borane-THF adduct are added and the mixture is stirred for a further 60 minutes. The reaction is stopped by addition of water, the organic phase is separated off and the aqueous phase is extracted three times with dichloromethane. The organic phase is dried and the solvent is removed under reduced pressure. Purification by means of chromatography gives the product in a yield of 80%.

$^1$H NMR (CDCl$_3$): δ=0.70 (q, 6H), 0.75 (s, 3H), 0.89 (ddd, 1H), 0.97 (t, 9H), 1.02 (s, 3H), 1.06 (dd, 1H), 1.17 (ddd, 1H), 1.80–0.5 (br, BH$_3$), 1.48–1.37 (m, 1H), 1.61 (dd, 1H), 1.66 (dd, 1H), 1.76 (ddd, 1H), 2.21 (dd, 1H), 2.83 (dd, 1H), 4.09 (dd, 1H), 7.53–7.31 (m, 6H), 7.62–7.54 (m, 2H), 7.89–7.82 (m, 2H)

$^{31}$P NMR (CDCl$_3$): δ=12.7 (d, 1P) ppm.

Example 5

(1 S,2R)-10-(Boranatodiphenylphosphino) isoborneol 11 mmol of tetrabutylammonium fluoride are added to a solution of 4.39 mmol of 10-boranatodiphenylphosphino-2-trimethylsilyloxyborane in 4 ml of THF and the solution is stirred for 90 minutes at room temperature. Water and dichloromethane are subsequently added, the organic phase is separated off and the aqueous phase is extracted three times with dichloromethane. After drying and evaporation of the solvent, the crude product is purified by means of chromatography. The product is obtained as a colorless solid in a yield of 94%.

$^1$H NMR (CDCl$_3$): δ=0.59 (ddd, 1H), 0.78 (s, 3H), 0.94–0.80 (m, 2H), 1.08 (s, 3H), 1.50–1.37 (m, 1H), 1.60–0.75 (br, BH$_3$), 1.63 (dd, 1H), 1.68 (dd, 1H), 1.78 (ddd, 1H), 2.33 (dd, 1H), 2.58 (dd, 1H), 3.10 (br, 1H), 4.14 (dd, 1H), 7.56–7.37 (m, 6H), 7.64–7.57 (m, 2H), 7.89–7.81 (m, 2H) ppm.

$^{31}$P-NMR (CDCl$_3$): δ=10.4 (d, 1P) ppm.

Example 6

(1 S,2R)-10-Boranatodiphenylphosphino-2-boranatodiphenylphosphinoxybornane n-Butyllithium is added dropwise to a solution of 0.28 mmol of 10-(boranatodiphenylphosphino)isoborneol in 4 ml of THF which has been cooled to −78° C. and the mixture is stirred for 1 hour. 0.34 mmol of chlorodiphenylphosphine is added to this solution, the mixture is stirred for 2 hours at −78° C. and a further 7 hours at room temperature, and the solution is subsequently refluxed for 2 hours. The reaction solution is cooled to 0° C. 0.60 mmol of borane-THF adduct is added to this solution and the mixture is stirred at 0° C. for 1 hour. The reaction is stopped by addition of water. The aqueous phase is extracted three times with dichloromethane. After drying and evaporation, the crude product is purified by means of chromatography and the product is obtained in a yield of 53%.

$^1$H-NMR (CDCl$_3$): δ=0.93–0.83 (m, 5H), 1.06 (s, 3H), 1.53–1.44 (m, 1H), 1.70–0.75 (Br, BH3), 1.70–1.57 m, 3H), 1.88 (ddd, 1H), 2.26 (dd, 1H), 2.79 (dd, 1H), 4.49 (ddd, 1H), 7.82–7.29 (m, 20H) ppm.

$^{31}$P-NMR (CDCl$_3$): δ=12.6 (s, 1P), 102.6 (d, 1P) ppm.

Example 7

(1 S,2R)-10-Diphenylphosphino-2-diphenylphosphinitobornane 2.72 mmol of (1S, 2R)-10-boranatodiphenylphosphino-2-boranatodiphenyl-phosphinoxybornane are dissolved in 75 ml of toluene and mixed with 10.8 mmol of DABCO. The solution is heated at 85° C. for 16 hours and the solvent is subsequently removed under reduced pressure. The product is taken up in ether/pentane (1:3), filtered through neutral aluminum oxide and the solvent is removed under reduced pressure. The product is obtained in a yield of 67%.

$^1$H-NMR (CDCl$_3$): δ=0.72 (s, 3H), 0.80 (m, 2H), 0.99 (m, 1H), 1.10 (s, 3H), 1.36 (m, 1H), 1.57 (m, 2H) 1.81 (m, 1H), 2.13 (dd, 1H), 2.27 (dd, 1H), 4.32 (ddd, 1H), 6.70–7.09 (m, 8H), 7.22–7.24 (m, 6H), 7.39–7.46 (m, 6H) ppm.

$^{31}$P-NMR (CDCl$_3$): δ=−24.0 (1P), 112.2 (1P) ppm.

Example 8

(1S,2R)-10-Diphenylphosphino-2-bis(3,5-dimethylphenyl)phosphinitobornane

The compound is prepared by a method analogous to examples 1–7 and the product is obtained in a yield of 61%.

$^1$H-NMR (CDCl$_3$): δ=0.82 (s, 3H), 1.33–0.84 (m, 15H), 1.12 (s, 3H), 2.79 (s, 12H), 4.32 (ddd, 1H), 7.62–6.81 (m, 16H) ppm.

$^{31}$P-NMR (CDCl$_3$): δ=−24.1 (1P), 112.6(1P) ppm.

Example 9

(1S,2R)-10-Diphenylphosphino-2-dicyclohexylphosphinitobornane

The compound was prepared by a method analogous to examples 1–7 and the product is obtained in a yield of 55%.

$^1$H-NMR (CDCl$_3$): δ=0.73 (s, 3H), 0.99 (s, 3H), 2.01–0.76 (m, 29H), 2.08 (dd, 1H), 2.34 (dd, 1H), 4.39 (m, 1H), 7.21–7.14 (m, 10H) ppm.

$^{31}$P-NMR (CDCl$_3$): δ=−25.6 (1P), 143.2 (1P) ppm.

Example 10

(1S,2R)-6-{1-[(Diphenylphosphinyl)methyl]-7,7-dimethylbicyclo[2.2.1]hept- 2-yloxy}-5,7-dioxa-6-phosphadibenzo[a,c]cycloheptene The compound was prepared by a method analogous to examples 1–7 and the product is obtained in a yield of 48%.

¹H-NMR (CDCl₃): δ=0.74 (s, 3H), 0.81 (m, 2H), 0.99 (m, 1H), 1.07 (s, 3H), 1.37 (m, 1H), 1.59 (m, 2H), 181 (m, 1H), 2.11 (dd, 1H), 2.27 (dd, 1H), 4.66 (ddd, 1H) 6.83 (m, 1H), 7.13–717 (m, 7H), 7.23–7.38 (m, 10H), 7.58 (m, 2H) ppm.

³¹P-NMR (CDCl₃): δ=−24.5 (1P), 151.4 (1P) ppm.

Hydrogenation Examples

General procedure for the hydrogenation of methyl acetamidocinnamate and methyl acetamidoacrylate 0.6 μmol of Rh(COD)₂OTf and 0.66 μmol of ligand are stirred in 1 ml of methanol for 10 minutes. 300 μmol of methyl acetamidocinnamate or methyl acetamidoacrylate (in 1 ml of methanol) are added to this solution. The reaction mixture is stirred for 2 hours in an autoclave at room temperature and under 5 bar of hydrogen. The reaction mixture is filtered through silica gel and the enantiomeric excess of the crude product is determined by means of HPLC.

General procedure for the hydrogenation of N-acetyyl-2-phenyl-1-ethenylamine 0.6 μmol of Rh(COD)₂OTf and 0.66 μmol of ligand are stirred in 1 ml of methanol for 10 minutes. 300 μmol of N-acetyl-2-phenyl-1-ethenylamine (in 1 ml of methanol) are added to this solution. The reaction mixture is stirred for 2 hours in an autoclave at 40° C. and under 10 bar of hydrogen. The reaction mixture is filtered through silica gel and the enantiomeric excess of the crude product is determined by means of HPLC.

Ligand

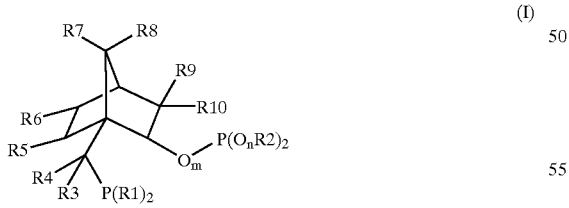

| R | Methyl acetamido-cinnamate (% ee) | N-acetyl-2-phenyl-1-ethenylamine (% ee) | Methyl acetamido-acrylate (% ee) |
|---|---|---|---|
| Ph | 46 | −16 | −88 |
| Cy | −3 | −89 | 6 |
| 3,5-Me—Ph | −18 | 7 | −94 |

What is claimed is:

1. A bidenate organophosphorus compound of formula (1), (I)

where m and n may each be, independently of one another, 0 or 1 and

R1–R2 are, independently of one another, radicals selected from the group consisting of C₁–C₂₄-alkyl, C₃–C₈-cycloalkyl in which one or two of the carbon atoms of the ring may be replaced by heteroatoms selected from the group consisting of N, O and S C₂–C₁₃-heteroaryl in which the number of heteroatoms selected from the group consisting of N, O and S may be 1–4, C₆–C₁₄-aryl, phenyl, naphthyl and fluorenyl radicals, where the abovementioned radicals may themselves each be substituted by, independently of one another, one or more substituents selected from the group consisting of hydrogen, C₁–C₂₀-alkyl, C₂–C₂₀-alkenyl, C₁–C₁₀-haloalkyl, C₃–C₈-cycloalkyl, C₂–C₉-heterocycloalkyl, in which the number of heteroatoms selected from the group consisting of N, O and S may be 1–4, C₆–C₈-aryl, phenyl, naphthyl, fluorenyl, C₂–C₆-heteroaryl, in which the number of heteroatoms selected from the group consisting of N, O and S may be 1–4, C₁–C₁₀-alkoxy, C₁–C₉-trihalomethylalkyl, halo, hydroxy, trifluoromethylsulfonato, oxo, amino, C₁–C₈-substituted amino of the formulae NH-alkyl-C₁–C₈, NH-aryl-C₅–C₆, N-alkyl₂-C₁–C₈, N-aryl₂-C₅–C₆, N-alkyl₃-C₁–C₈⁺, N-aryl₃-C₅–C₆⁺, NH—CO-alkyl-C₁–C₈, NO—CO-aryl-C₅–C₆, cyano, carboxylato of the formulae COOH and COOQ, where Q is either a monovalent cation or C₁–C₈-alkyl, C₁–C₆-acyloxy, sulfinato, sulfonato of the formulae SO₃H and SO₃Q, where Q is either a monovalent cation, C₁–C₈-alkyl or C₆-aryl, phosphate of the formulae PO₃H₂, PO₃HQ and PO₃Q₂, where Q is either a monovalent cation, C₁–C₈-alkyl or C₆-aryl, tri-C₁–C₆-alkylsilyl radicals, where the two radicals R1 or the two radicals R2 may be bridged, where the resulting ring may be substituted by linear or branched C₁–C₁₀-alkyl, C₆-aryl, benzyl, C₁–C₁₀-alkoxy, hydroxy or benzyloxy groups, and where R3–R10 may each be, independently of one another, a hydrogen atom or a C₁–C₂₄-alkyl, C₁–C₁₀-haloalkyl, C₃–C₈-cycloalkyl, C₃–C₈-cycloalkenyl group, where one or two carbon atoms of the cycloalkyl or cycloalkenyl may also be replaced by heteroatoms selected from the group consisting of N, O and S, C₆–C₁₄-aryl, phenyl, naphthyl, fluorenyl or C₂–C₁₃-heteroaryl group in which the number of heteroatoms selected from the group consisting of N, O and S may be 1–4, where the abovementioned groups may themselves each be, independently of one another, monosubstituted or polysubstituted by hydrogen, C₁–C₂₀-alkyl, C₂–C₂₀-alkenyl, C₁–C₁₀-haloalkyl, C₃–C₈-cycloalkyl, C₃–C₈-cycloalkenyl, C₂–C₉-heteroalkyl, C₁–C₉-heteroalkenyl, C₆–C₈-aryl, phenyl, naphthyl, fluorenyl, C₂–C₆-heteroaryl in which the number of heteroatoms, in particular from the group consisting of N, O and S may be 1–4, C₁–C₁₀-alkoxy, trifluoromethyl, fluoro, oxo, amino, C₁–C₈-substituted amino radicals of the formulae N-alkyl₂-C₁–C₈, N-aryl₂-C₅–C₆, N-alkyl₃-C₁–C₈⁺, N-aryl₃-C₅–C₆⁺, and where two of these substituents may also be connected, and where P is trivalent phosphorus.

2. The compound as claimed in claim 1, wherein R7 and R8 are methyl and R3–R6 and R9–R10 are hydrogen, in said compound of formula (I).

3. The compound as claimed in claim 1, wherein the substituents R1 and R2 are each, independently of one another, 1-methylethyl, cyclohexyl, cyclopentyl, phenyl, 2-methylphenyl, 3,5-dimethylphenyl, 4-methylphenyl, 4-methoxyphenyl, 3,5-bis(trifluoromethyl)phenyl, 4-trifluoromethylphenyl, 3,5-dimethyl-4-methoxyphenyl, 4-phenoxyphenyl, 4-dialkylaminophenyl, 2-alkylphenyl, 3-alkylphenyl, 4-alkylphenyl, 2,6-dialkylphenyl, 3,5- dialkylphenyl, 3,4,5-trialkylphenyl, 2-alkoxyphenyl, 3-alkoxyphenyl, 4-alkoxyphenyl, 2,6-dialkoxyphenyl, 3,5-dialkoxyphenyl, 3,4,5-trialkoxyphenyl, 3,5-dialkyl-4-alkoxyphenyl, 3,5-dialkyl-4-dialkylaminophenyl, 4-dialkylamino, 3,5-trifluoromethyl, 4-trifluoromethyl, 2-sulfonyl, 3-sulfonyl, 4-sulfonyl, monohalogenated to tetrahalogenated phenyl and naphthyl, in said compound of formula (I).

4. The compound as claimed in claim 1, wherein said compound of formula (I) is enantiomerically enriched.

5. The compound as claimed in claim 4, wherein said compound of formula (I) is at least 90% enantiomerically enriched.

6. A complex obtained by mixing a transition metal salt or a transition metal precursor complex with at least one bidentate organophosphorus compound of the formula (I) as claimed in claim 1.

7. A complex of the formula (II)

[M$_x$P$_y$L$_z$S$_q$]A$_r$  (II)

wherein

M is a transition metal center,

L are identical or different coordinating organic or inorganic ligands,

S are coordinating solvent molecules and

A are equivalents of noncoordinating anions, where x is 1 or 2, y is an integer greater than or equal to 1, z, q and r are integers greater than or equal to 0, where the upper limit on the sum y+z+q is imposed by the number of coordination centers available on the metal centers but not all coordination sites have to be occupied, wherein P are bidentate organophosphorus compounds of the formula (I) as claimed in claim 1.

8. The complex as claimed in claim 6, wherein said complex comprises a transition metal selected from the group consisting of Ru, Co, Rh, Ir, Ni, Pd, Pt, Cu.

9. A process for preparing a bidentate organophosphorus compound of formula (I) as claimed in claim 1 wherein n=1, comprising a) replacement of the 10-sulfonic acid radical of a 10-camphorsulfonic acid derivative by a halide radical by mixing a 10-camphorsulfonic acid derivative and a phosphorus trihalide or a molecular halogen in the presence of a phosphine, b) silylation of the resulting hydroxy group of the 10-halocamphor derivative, c) phosphination of the 10-halocamphor derivative by replacement of the halogen radical by a phosphine group by addition of an alkaline metal salt of a phosphine, d) conversion of the intermediate into a borane complex by addition of a borane adduct, e) removal of the protective silyl group, f) basic phosphination of the hydroxy group by addition of a phosphine halide, and g) removal of the protective borane group by addition of a nitrogen-containing base.

10. A process for preparing the bidentate organophosphorous compounds of the formula (I) as claimed in claim 1 wherein n=0, said process comprising thermally rearranging the phosphine group of a phosphine phosphinite to a phosphine oxide, then reducing said phosphine oxide to a diphosphine.

11. A method for asymmetric reaction or polymerization, comprising reacting a compound in an asymmetric reaction in the presence of the complex claimed in claim 6.

12. A method for asymmetric reaction or polymerization, comprising reacting a compound in an asymmetric reaction in the presence of the complex claimed in claim 7.

13. The method as claimed in claim 11, wherein the asymmetric reaction is a reaction selected from the group consisting of hydrogenation, hydroformylation, rearrangement, allylic alkylation, cyclopropanation, hydrosilylation, hydride transfer, hydroboration, hydrocyanation, hydrocarboxylation, aldol reaction, a Pauson-Khand reaction and a Heck reaction.

14. The method as claimed in claim 12, wherein the asymmetric reaction is a reaction selected from the group consisting of hydrogenation, hydroformylation, rearrangement, allylic alkylation, cyclopropanation, hydrosilylation, hydride transfer reactions, hydroborations, hydrocyanation, hydrocarboxylations aldol reaction, a Pauson-Khand reaction and a Heck reaction.

15. The method as claimed in claim 13, wherein the asymmetric reaction is hydrogen or hydroformylation.

16. The method as claimed in claim 14, wherein the asymmetric reaction is hydrogen or hydroformylation.

17. The complex as claimed in claim 7, wherein said transition metal is a metal selected from the group consisting of Ru, Co, Rh, Ir, Ni, Pd, Pt, and Cu.

* * * * *